United States Patent
Ragain, Jr. et al.

(10) Patent No.: US 8,053,487 B2
(45) Date of Patent: Nov. 8, 2011

(54) MULTIFUNCTIONAL ACRYLATES USED AS CROSS-LINKERS IN DENTAL AND BIOMEDICAL SELF-ETCHING BONDING ADHESIVES

(75) Inventors: James C. Ragain, Jr., LaFollette, TN (US); Amer Tiba, Lake Bluff, IL (US); David G. Charlton, Gurnee, IL (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 269 days.

(21) Appl. No.: 12/362,622

(22) Filed: Jan. 30, 2009

(65) Prior Publication Data

US 2010/0197825 A1    Aug. 5, 2010

(51) Int. Cl.
*A61K 6/083* (2006.01)
*G03F 7/029* (2006.01)
*C08G 59/68* (2006.01)
*C09K 3/00* (2006.01)
*A61C 5/00* (2006.01)

(52) U.S. Cl. ........... 522/77; 522/48; 522/13; 106/35; 433/228.1

(58) Field of Classification Search .......... 522/13, 522/48, 77; 106/35; 433/228.1
See application file for complete search history.

(56) References Cited

U.S. PATENT DOCUMENTS

| | | |
|---|---|---|
| 2003/0180691 A1 | 9/2003 | Hamer et al. |
| 2004/0039078 A1 | 2/2004 | Suh et al. |
| 2005/0028705 A1 | 2/2005 | Wagh et al. |
| 2006/0189728 A1 | 8/2006 | Qian |
| 2006/0247330 A1* | 11/2006 | Takano et al. ........ 523/116 |
| 2007/0049656 A1 | 3/2007 | Jia et al. |
| 2007/0197683 A1 | 8/2007 | Jia et al. |
| 2009/0018234 A1* | 1/2009 | Tokui et al. ........ 523/116 |

* cited by examiner

*Primary Examiner* — Milton I Cano
*Assistant Examiner* — Jessica Paul
(74) *Attorney, Agent, or Firm* — Joseph K. Hemby; Albert M. Churilla; Ning Yang

(57) ABSTRACT

This invention describes an adhesive used for bonding dental and medical biomaterials to hard tissues via a molecular bridge formed from calcium-reactive amines and acrylic or methacrylic ester monomers to hard tissues such as enamel, dentin, and bone. This formulation consists of an acid-stable polymerizable compound with multi-functional acrylate cross-linkers. This formula provides good self-adherence without prior preparation of the hard tissue substrates. The formulation can contain chemical- and/or light-activated free-radical initiators.

4 Claims, No Drawings

MULTIFUNCTIONAL ACRYLATES USED AS CROSS-LINKERS IN DENTAL AND BIOMEDICAL SELF-ETCHING BONDING ADHESIVES

BACKGROUND OF INVENTION

1. Field of Invention

This invention relates to a biomaterial and more specifically a high molecular weight, multifunctional acrylate cross-linking composition that, when formulated with other compounds will self-etch and self-adhere to hard tissues, such as enamel, dentin, and bone.

2. Description of the Related Art

The use of synthetic materials to expedite healing is becoming more widespread. A burgeoning area of growth is the use of relatively inert hardening agents for use as adhesives or as a substitute for hard tissue. Hard tissue typically means tissues that have become mineralized, or tissue having a firm intercellular substance, such as enamel, dentin, cartilage, and bone. Bone and tooth structure, such as enamel, dentin and cementum, have certain compositional and morphologic similarities. Like enamel and dentin, bone consists primarily of inorganic material, which is almost exclusively in the form of an apatite of calcium and phosphate that resembles hydroxylapatite, and a lesser amount of organic material, which is 90% collagen. Morphologic similarities also exist. Enamel and dentin both contain tubules which meet their respective surfaces at a perpendicular angle, while bone contains tube-like Haversian Canals. The Haversian Canals run parallel to the bone's surface, but Volkmann's Canals, which run from them meet the bone surface at a perpendicular angle.

Teeth that are fractured or have lost dental restorations often involve exposed dentin. These exposed teeth are prone to tooth decay, and patients usually experience pain. For treatment purposes, the exposed teeth are usually restored with permanent dental restorations. However, definitive dental restorations often are not performed in a timely fashion. In these cases, temporary dental restorations (fillings) are usually placed onto the exposed teeth. There are a variety of restorative dental materials that can be used as temporary fillings.

The materials most commonly chosen as temporary fillings are zinc oxide-eugenol (ZOE) compounds, glass-ionomer materials, and resin-based dental materials. These filling materials are retained in teeth through mechanical retention and/or chemical bonding with the tooth structure.

ZOE fillings require mechanical retention. These materials are relatively weak compared to the other types of temporary filling materials.

Glass-ionomer dental filling materials can bond to tooth structure without the need of a separately applied bonding agent. In addition, glass-ionomer materials release fluoride, which strengthens the surface of the tooth. A disadvantage of glass-ionomer dental filling materials is their relatively long setting time and concomitant sensitivity to moisture. Moisture exposure can result in premature disintegration of the glass-ionomer material and reduce bond strength. Furthermore, the chemical bond formed between glass-ionomers and tooth structure is relatively weak.

Resin-based filling materials can be bond to teeth using both mechanical and chemical retentions. Bonding of resin-based dental materials to tooth structure is currently achieved through a multi-step process. A dentin-enamel bonding agent must be applied to the tooth prior to placing the dental material. Applying this bonding agent often requires multiple steps and a significant amount of clinical time. Misapplication of the bonding material may also occur.

In general, retention of temporary fillings through chemical bonding is quicker, requires less preparation of the tooth, and is usually stronger. Often teeth can be temporarily restored with dental materials using only chemical bonding. Acid etching of the tooth surface are often performed to improve adhesion of resin-based filling materials by promoting mechanical retention. However, many acid-etching agents must be removed prior to application of the bonding agents, which further increases clinical time. Acid etching can also cause dental sensitivity in some patients.

There are dental restorative materials on the market that are self-etching adhesives. These compositions generally use water and/or organic solvents and take a liquid form. Consequently, these self-etching adhesives have a short shelf-life, which may pose additional problems for storage. For example, these materials may experience a premature setting in extreme conditions such as those presented in a desert battlefield. Furthermore, many of these formulations require multiple applications of a single component or application of several separate components. Therefore, they require more clinical time to apply than the inventive formulation.

U.S. Pub. No. 2007/0244215 A1 by Junjie Sang, describes a one-component self-etching dental adhesive, which requires a simple one-coat application, without the need of separate acid-etching, priming or bonding step. This is achieved through the employment of a hydrolytically stable, acidic, high-strength adhesive monomer (such as PENTA) with a stable, bifunctional, hydrophilic monomer (such as AHPMA) that yields greater cross-linking. However, this material lacks filler content and does not provide a fluoride source.

U.S. Pub. No. 2007/0155853 A1 by Chen et al., is another one-component self-etching self-priming dental adhesive composition. The formulation contains BisGMA (2,2-bis[4-(2-hydroxy-3-methacryloylpropoxy)-phenyl]-propane), DPPA (dipentaerythrytol pentaacrylate), GDM (glycerol dimethacrylate), GPDM (glycerol phosphate dimethacrylate), and PMGDM (pyromellitic glycerol dimethacrylate). The formulation contains both water and an organic solvent such as acetone or ethanol. Additional clinical steps and resin materials are required to bond composite resins to dentin or enamel.

U.S. Pub. No. 2006/0069181 by Thalaker et al. presents a liquid self-etch adhesive that is composed of a carboxylic acid functional polymer and water. This dental adhesive composition consists of two liquid components and contains no fluoride releasing agents or glass fillers. Additional clinical steps and resin materials are required to bond composite resins to dentin or enamel.

U.S. Pub. No. 2007/0248927 A1 by Luchterhandt et al. is a self-adhesive composition based on polyacrylate, Kayamer, MH-P (Methacryloxyhexyl phosphate), MO-P (8-Methacryloxyoctyl phosphate), and MD-P (10-Methacryloxydecyl phosphate) polymerizable compounds. This formula is only photo-curable and requires additional priming step and curing equipment.

U.S. Pub. No. 2007/0203257 A1 by Xuejun Qian, describes a two-part paste/paste self-etch adhering dental composition based on UDMA (reaction product of 2-hydroxyethyl methacrylate with 2,4,4-trimethylhexane diisocyanate), BisGMA, GDM-P (glyceryldimethacrylate phosphate), and GDM (glyceryidimethacrylate). It also contains a solvent, which may increase the oxidation rate of the formula. The formula does not contain any fluoride releasing agent.

U.S. Pub. No. 2005/0277706 A1 by Han et al., describes a highly functional dental adhesive that is based on multifunctional pre-polymer mixture of BisGMA, Tri-GMA, 4-MBTA (4-methacryloxybutyltrimellitic anhydride), MDP, HPMA and water. This adhesive is only photo-curable, which requires additional curing equipment. In addition, this formula contains a maximum of five percent filer material and does not include a fluoride releasing agent.

SUMMARY OF THE INVENTION

The current invention aims to improve existing technology. The inventive formulation has multiple advantages over the prior art. It is a self-etching material, which can be applied to tooth in a single step without the need of a primer. The inventive formulation is also dual-curable, which means it can be photo-cured or chemically hardened. Chemical setting allows for curing in deep areas where light is not effective and eliminates the need of additional equipment in situations where such equipment are not readily available. Furthermore, the inventive formula contains fluoride releasing materials and up to 75% of glass fillers in a combination of different particle sizes. The inclusion of fluoride releasing agent and high percentage of glass particles of varying sizes improve physical and mechanical properties of the final set material. Additionally, the inventive formula is a power and liquid combination format and contains no solvent, which may increase shelf-life and prevents premature setting.

An object of this invention is an acid-stable polymerizable composition with multi-functional acrylate cross-linkers suitable as a dental/biomedical self-adhesive bonding material.

Another object of the invention is a self-etching, acid-stable polymerizable composition with multifunctional acrylate cross-linkers, which provides good self-adherence without prior preparation of the hard tissue or the substrates.

An additional object of the invention is a self-etching, acid-stable polymerizable adhesive material, which contains chemical and/or light-activated free-radical initiators that allows the final material to set within a relatively short time, approximately 4-4.5 minutes at 37° C.

A further object of the invention is a fluoride-releasing composition that can be used as a self-etching, self-adhesive bonding agent between hard tissues (enamel, dentin, or bone) and dental and biomedical substrates.

Another object of this invention is a method of bonding dental and medical biomaterials via a molecular bridge formed from calcium reactive amines and acrylic or methacrylic ester monomers to hard tissues such as enamel, dentin, and bone.

DETAIL DESCRIPTION OF THE INVENTION

This invention is directed to an adhesive composition that can be used in bonding dental and medical biomaterials to hard tissues via a molecular bridge formed from calcium reactive amines and acrylic or methacrylic ester monomers contained in the biomaterials and enamel, dentin, and bone. The adhesive composition may be used as: (i) temporary dental restorative or dressing material, (ii) long-term dental restorative (filling) material through the incorporation of various inorganic filler materials, (iii) luting cement, for bonding fixed dental prosthetic devices, such as crowns and bridges, to dentin and enamel, or (iv) luting cement for bonding orthodontic brackets to enamel; (v) stint for stabilizing avulsed, inverted, or luxated teeth; (vi) bone cement, for bonding implant prostheses and skull implants to bone; (vii) liner or base under amalgam dental restorations.

This adhesive composition comprises of an acid-stable polymerizable compound with multi-functional acrylate cross-linkers and provides good self-etching and self-adherence without prior preparation of the hard tissue substrates, such as separate acid etching or priming steps. In general, the adhesive composition comprises a mixture of one or more polymerizable acrylic or methacrylate compounds, one or more hydrophilic acrylate or methacrylate compounds, one or more calcium reactive amines, one or more acrylic or methacrylic esters, one or more polymerization initiators, glass powder, fluoride-containing compounds, and other filter materials. The esters functions both as an acrylic or methacrylate compound that polymerizes with the other a acrylic or methacrylate compounds and as a cross-linker, which forms a salt bridge with calcium in the dentin or enamel. The preferred composition could vary slightly for different dental and biomedical applications. Considerations would include varying the formula to affect properties such as viscosity, flowability, working time, setting time, film thickness, and bond strength. Standard mechanical and material testing may be performed to assess these formulations for their designed application. In general, the laboratory tests that may be performed to measure the physical and mechanical properties of the inventive compound, which include compressive strength, DTS, flexural strength, shear bond strength, and film thickness. One of skill in the art will appropriate that the above material properties can be adjusted as appropriate for each dental/biomedical application.

In a preferred embodiment, the composition contains two components: a liquid component and a powder component. The liquid component contains at least one polymerizable acrylic or methacrylate compound, and one or more hydrophilic acrylate or methacrylate compounds. Examples of suitable hydrophilic acrylates are 2-hydroxyethyl acrylate and hydroxypropyl acrylate. An example of a hydrophilic methacrylate compound is hydroxyethylmethacrylate (HEMA). Examples of polymerizable acrylates are: ethyl acrylate, propyl acrylate, isopropyl acrylate, 2-hydroxyethyl acrylate, hydroxypropyl acrylate, tetrahydrofurfuryl acrylate, glycidyl acrylate, glycerol mono- and di-acrylate, ethyleneglycol diacrylate, polyethyleneglycol diacrylate, neopentyl glycol diacrylate, trimethylolpropane triacrylate, mono-, di-, tri-acrylate, mono-, di-, tri-, and tetra-acrylates of pentaerythritol and dipentaerythritol, 1,3-butanediol diacrylate, 1,4-butanedioldiacrylate, 1,6-hexane diol diacrylate, 2,2'-bis[3(4-phenoxy)-2-hydroxypropane-1-acrylate]propane, 2,2'bis(4-acryloxyphenyl)propane, 2,2'-bis[3(4-phenoxy)-2-hydroxypropane-1-acrylate]propane, dipentaerthritol pentaacrylate esters (SR 399) and dipentaerthritol pentaacrylate esters (SR 399 LV).

Polymerizable methacrylate compounds may be: methacrylates, ethyl methacrylate, propyl methacrylate, isopropyl methacrylate, tetrahydrofurfuryl methacrylate, glycidyl methacrylate, the diglycidyl methacrylate of bis-phenol A (2,2-Bis[4-(2-hydroxy-3-methacryloxypropoxy)phenyl]propane) (BisGMA), glycerol mono- and di-methacrylate, ethyleneglycol dimethacrylate, polyethyleneglycol dimethacrylate, triethylene glycol dimethacrylate (TEGDMA), neopentylglycol dimethacrylate, trimethylol propane trimethacrylate, mono-, di-, tri-, and tetra-methacrylates of pentacrythritol and dipentaerythritol, 1,3-butanediol dimethacrylate, 1,4-butanediol dimethacrylate, Bis[2-(methacryloyloxy)ethyl]phosphate (BisMEP), 1,6-hexanediol dimethacrylate, 2-2'-bis(4-methacryloxypheny)propane, 2,2'-bis[4(2-hydroxy-3-methacryloxy-phenyl)]propane, 2,2' bis[4(2-hydroxy-3acryloxyphyenyl) propane, 2,2'-bis(4-methacryloxyethoxypheny)propane, 2,2'-bis(4-acryloxyethoxyphenyl)propane, 2,2'-bis(4-methacryloxypropoxyphenyl)propane, 2,2'-bis(4-acryloxypropoxyphenyl) propane, 2,2'-bis(4-methacryloxydiethoxyphenyl)propane, 2,2'-bis(4-acryloxydiethoxyphenyl)propane, 2,2'-bis[3(4-phenoxy)-2-dydroxypropane-1-methacrylate]propane.

The liquid component also contains an amine that is capable of forming a salt bridge between the calcium ions in the dentin and acrylic or methacrylic esters. An example of a methacrylate ester is Bis[2-(methacryloyloxy)ethyl]phosphate (BisMEP). The preferred amines include but are not limited to aromatic amines such as 4-(dimethylamino) benzoic acid (DMABA) and ethyl 4-dimethylaminobenzoate (EDMAB). The selection of the appropriate amine is critical. Unlike other amines found in other dual-cure (chemical- and visible-light photo-curing functions together in one formulation) and photo-cure dental and biomedical adhesive materials, the amine used in the preferred embodiment (EDMAB) is stable in an acidic environment. Furthermore, although some aromatic amines, such as DMABA and EDMAB, have been experimentally determined to be effective at permitting adherence of the polymerizable acrylate to dentin, others, such as 2,2'-(p-tolylimino) diethanol (P-TID) is not effective.

In addition to the acrylates and amines, the liquid component of the inventive formulation contains one or more acrylic ester or methacrylic ester. The esters function as an ester and as an acrylic or methacrylate compound and form a cross-link between the polymerizable acrylic or methacrylate compounds. In the preferred embodiment, dipentaerthritol pentaacrylate esters (SR 399 LV) are used as this cross-linker. SR 399 LV is stable in an acid-polymerizable formula that contains an acid such as Bis[2-(methacryloyloxy)ethyl]phosphate (BisMEP) and an amine base such as ethyl-4-dimethylaminobenzoate (EDMAB). SR 399 LV is easily blended and co-polymerized with other methacrylates, such as 2,2-Bis[4-(2-hydroxy-3-methacryloxypropoxy)phenyl]propane (BisGMA), hydroxyethylmethacrylate (HEMA) and triethyleneglycol dimethacrylate (TEGDMA), in the polymerizable formula. The incorporation of dipentaerthritol pentaacrylate esters (SR 399 LV) would self-etch hard tissues (such as enamel, dentin, and bone) and crosslink the resin matrix upon setting, which enhances the resin matrix upon polymerization (setting).

The powder component of the inventive composition contains many filler materials, which include glass powder of various particles sizes and one or more fluoride releasing agents. The glass particles not only improve the physical and mechanical properties of the composition but also serve as the base for the acid-base reaction. The powder component may also contain other filler materials such as Barium, Aerosil 200, Pigments, Silica, Alumina, Aluminum Fluoride, Calcium Fluoride, Sodium Fluoride, Aluminum Phosphate, Calcium, Strontium, Zinc, Sodium, Potassium, Lanthanum, Alumino-silicates, other metal oxides, metal fluorides and metal phosphates The adhesive composition also uses at least one initiator to permit photo or chemical initiation of curing, which could be incorporated into either the liquid component or the powder component. The formulation may, additionally, contain a co-initiator to accelerate the curing process. In the preferred embodiment, both a light-curing initiator camphorquinone (CQ) and a self-curing initiator BPO are used. A curing inhibitor, such as BHT, may also be included in the adhesive composition in order to have a more controlled setting time.

Despite the chemicals identified in the preferred embodiments, the inventive formulation also contemplates that other chemicals, with similar characteristics, can be used. For example, in place of BisMEP, 4 methacryloxyethyltrimellitic anhydride, biphenyldimethacrylate, ethylene glycol methacrylate phosphate or other esters of methacrylate can be used. Similarly, other photo-initiators or chemical initiators, other than CQ can be used, such as diphenyl(2,4,6-trimethylbenzoyl) phosphine oxide. Also, in place of DMABA, other amines could be substituted, such as ethyl 4-dimethylaminobezoate (EDMAB). Similarly, urethanedimethacrylate can be substituted for BisGMA. Other dimethacrylate or multimethacrylate diluents can be used instead of TEGDMA, such as trimethylpropane trimethacrylate.

For either dental or biomedical applications, each compound of the preferred formulation will fall within the following ranges by weight.

Liquid Part

| Chemical | Formulation weight range (%) |
| --- | --- |
| HEMA | (20-50) |
| TEGDMA | (10-30) |
| BisMEP | (5-25) |
| SR 399 LV | (5-25) |
| BisGMA | (5-30) |
| EDMAB | (1-8) |
| CQ | (0.1-0.8) |
| BHT (inhibitor) | (0.01-0.06) |

Powder Part:

| Chemical | Formulation weight range (%) |
| --- | --- |
| GI SP2034 | (70-95) |
| BPO | (1-5) |
| Ba Glass | (1-5) |
| Aerosil 200 | (1-5) |
| Pigment | (0.001-0.01) |

Paste:

The powder and liquid were mixed in a powder:liquid ratio of 3:1 by weight to form a paste and chemically hardened (set) 4 to 4.5 minutes later at 37° C. Although, the inventive adhesive composition may be used for many dental and medical applications, for illustrative purposes, the following examples shows the inventive adhesive material being used as a dental restoration materials and as luting cement. A preferred formulation of the invention composition for use as a dental restorative and luting cement includes the following in the liquid and powder components:

Liquid Component

| Acronym | Full Chemical Name | Source | Preferred Percentage by Weight |
| --- | --- | --- | --- |
| HEMA | Hydroxyethylmethacrylate | Aldrich ® | 33.68% |
| TEGDMA | Triethyleneglycol dimethacrylate | Aldrich ® | 20.00% |
| BisMEP | Bis[2-(methacryloyloxy)ethyl]phosphate | Aldrich ® | 20.00% |

-continued

| Acronym | Full Chemical Name | Source | Preferred Percentage by Weight |
|---|---|---|---|
| SR 399 LV | Dipentaerthritol pentaacrylate esters | Sartomer ™ | 10.00% |
| BisGMA | 2,2-Bis[4-(2-hydroxy-3-methacryloxypropoxy)phenyl]propane | Aldrich ® | 10.00% |
| EDMAB | Ethyl-4-Dimethylaminobenzoate | Aldrich ® | 6.00% |
| BHT | 2,6-Di-tert-butyl-4-methylphenol | Aldrich ® | 0.02% |
| CQ | Camphorquinone | Aldrich ® | 0.30% |
| | | | Total = 100% |

Powder Component

| Acronym | Full Chemical Name | Source | Preferred Percentage by Weight |
|---|---|---|---|
| GI SP2034 | Glass powder TF grind | Specialty Glass Products Inc. | 93.998% |
| Pigment | Phthalocyanine green 7 | Ultradent Products Inc. | 0.002% |
| BPO | Dipentaerthritol pentaacrylate esters | Aldrich ® | 2.00% |
| Ba Glass | 7% silanated 0.7 μm Ba glass | Esstech, Inc. | 2.00% |
| Aerosil 200 | Aerosil A200 | Degussa | 2.00% |
| | | | Total = 100% |

It is relatively easy to prepare compounds from this formula. The powder and liquid were mixed in a powder:liquid ratio of 3:1 by weight. Mixing requires thorough incorporation and blending of the separate powder and liquid components. After mixing, the paste sets (hardens) by way of an acid/base reaction and a free-radical polymerization reaction in 4 to 4.5 minutes at 37° C.

When used as dental restorative, the liquid and powder components may be mixed and applied to the tooth structure immediately in one step and simply wait for the restorative to set. Alternatively, the liquid and powder components may be mixed and placed onto the tooth in an incremental fashion. For example, mixing a small amount of power and liquid components in the same 3:1 ratio by weight and apply the paste to the tooth surface. Once the layer of paste hardens, a subsequent coat of adhesive may be mixed and applied to the tooth. This incremental build-up of adhesive materials allows the tooth to be restored its physiological shape.

EXAMPLE 1

Properties of the Adhesive Composition as Dental Restorative Materials

The preferred inventive formulation is tested in the lab as a dental restorative material. Laboratory tests shows that the incorporation of the multi-functional acrylate cross-linking compound dramatically enhanced the physical and mechanical properties of the final set in the prototype dental material. When using this formula as a bonding agent, the clinical pre-treatment techniques of acid etching and priming the tooth structure are not necessary. The material was tested against other classes of dental materials commonly used as temporary fillings. Those materials were FUJI IX™ GP fast (GC America, Ill.), KETAC-MOLAR™ (3M™ ESPE, Minn.), and IRM (Dentsply Caulk, Del.). The tests used were hardness (Knoop), compressive strength, diametral tensile strength (DTS), flexural strength, and dentin shear bond strength. Table 1 below provides the results of those tests.

TABLE 1

Physical property tests of inventive formulation as applied to a dental dressing.

| Dental Material | Hardness (KHN) | Compressive Strength (MPa) | DTS (MPa) | Flexural Strength (MPa) | Shear Dentin Bond Strength (MPa) |
|---|---|---|---|---|---|
| Inventive formulation | 36.6 (3.3) | 162.9 (19.2) | 27.67 (2.3) | 82.1 (5.3) | 12.2 (4.2) |
| FUJI IX ™ GP | 51.9 (2.3) | 167.8 (29.4) | 18.8 (3.8) | 18.2 (3.2) | 6.0 (2.0) |
| IRM ® | 11.4 (1.6) | 57.8 (10.9) | 7.9 (0.9) | 15.9 (1.7) | Not tested |
| KETAC-MOLAR ™ | 45.1 (9.4) | 149.1 (40.8) | 24.8 (4.3) | 17.3 (6.7) | 3.9 (1.2) |

The inventive formulation proved to have properties that were comparable or better than those of the materials tested. Placement of the inventive formulation on teeth requires minimal surface preparation and fewer steps for application, such as acid etching, priming, or use of bonding agents, resulting in less clinical time. In addition, the inventive formulation releases fluoride. Table 2 presents the results of fluoride-release tests.

TABLE 2

Cumulative fluoride release after 385 hours.

| Dental Material | Fluoride (ppm) |
| --- | --- |
| Inventive Formulation | 159.10 |
| FUJI IX ™ GP | 176.05 |
| Ketac-Bond | 201.29 |
| IRM ® | 0 |

Method of Use as Luting Cement for Bonding Fixed Dental Prosthetic Devices:

The inventive formulation may also be used as luting cement, for bonding fixed dental prosthetic devices, such as inlays, onlays, laminate veneers, bridges and crowns (including porcelain and porcelain fused to metal restorations), to dentin and enamel.

EXAMPLE 2

Properties as Luting Cement for Bonding Ceramic Dental Prosthetic Devices

The preferred formulation of the inventive composition previously stated was also tested as luting cement for bonding fixed dental prosthetic devices.

Shear bond strengths (SBS) of DENTSTAT™ (the preferred inventive formulation) and five commercially available luting cements to three types of ceramic substrates were determined (Table 3). Ten specimens of each material were tested.

TABLE 3

Luting cements and ceramic materials used in this study.

| | Manufacturers |
| --- | --- |
| Luting cements | |
| DENTSTAT ™ | Ultradent Products, Inc, South Jordan, UT |
| MultiLink Automix | Ivoclar/Vivadent, Schaan, Liechtenstein |
| Aegis C&B | BOSWORTH ® Co., Skokie, IL |
| PANAVIA 21 ® | Kuraray America Inc, New York, NY |
| Maxcem | Kerr Co, Orange, CA |
| NX3 | Kerr Co, Orange, CA |
| Ceramic materials | |
| IPS Empress CAD | Ivoclar/Vivadent, Schaan, Liechtenstein |
| Vitablocs Mark III | Vident, Brea, CA |
| Paradigm C | 3M ™/ESPE Corporation, St. Paul, MN |

Ceramic blocks provided by the manufacturers were used without mechanical modification. All ceramic surfaces were treated using porcelain etching gel (Pulpdent Co. Watertown, Mass.) and silanated following the manufacturers' instructions.

A #4 gelatin capsule (Torpac, Inc., Fairfield, N.J.) was half-filled with a resin composite (P60, 3M™ ESPE, St. Paul, Minn.) and light activated for 40 seconds using a curing light (Spectrum 800, Dentsply/Caulk, Milford, Del.). The remainder of the capsule was filled with the dental luting cement being tested, placed against the ceramic test surface, and stabilized with finger pressure. Excess material was removed from the base of the capsule, and the luting cement was allowed to set at room temperature (23±1° C.) for 10 minutes. The specimens were stored in 37±1° C. deionized water for 24 hours.

The specimens were tested to failure in shear with a testing machine (MTS, Alliance RT/5, MTS Corporation, Eden Prairie, Minn.) using a crosshead speed of 0.5 mm/min. Mean shear bond strengths (SBS) and standard deviations were calculated, and means were analyzed statistically using one-way ANOVA and Tukey's Test. The mode of failure was determined for each specimen by visual examination.

The results are presented in the Table 4. Failures occurred all within the ceramic materials. The mean SBS for DENTSTAT™ was not significantly higher than the SBS for MultiLink Automix when bonding to IPS Empress CAD and Paradigm C. However, the SBS of DENTSTAT™ was significantly higher than other luting cements when bonding to Vitablocs Mark III. Therefore, the SBS of DENTSTAT™ to all three ceramic substrates were comparable to or greater than the other luting cements tested.

TABLE 4

Shear bond strength, means (st. dev.), MPa, n = 10.
The SBS of materials with the same letter within a column
are not significantly different (p > 0.05)

| | IPS Empress CAD | Vitablocs Mark III | Paradigm C |
| --- | --- | --- | --- |
| DENTSTAT ™ | 25.3 (3.72) A | 20.2 (4.59) A | 22.2 (3.90) A |
| MultiLink Automix | 21.5 (4.98) A | 11.8 (3.76) B | 18.8 (4.34) A, B |
| Aegis C&B | 12.8 (2.88) B, C | 12.7 (2.35) B | 14.2 (3.01) B, C |
| PANAVIA 21 ® | 12.3 (2.18) B, C | 13.0 (2.80) B | 14.0 (4.12) B, C |
| Maxcem | 12.5 (4.21) B, C | 11.6 (2.79) B | 13.2 (3.50) C |
| NX3 | 12.0 (1.99) B, C | 12.4 (4.28) B | 12.1 (2.68) C |

EXAMPLE 3

Properties as Luting Cement for bonding Fixed Metal Dental Prosthetic Devices

The shear bond strengths (SBS) of DENTSTAT™ and five commercially available luting cements to three metal substrates were determined (Table 5). Metal alloy specimens (approximately 8 mm long, 8 mm wide and 4 mm thick) were fabricated per manufacturers' instructions using the lost wax technique. The metal specimens were mounted in autopolymerizing acrylic resin using cylindrical polytetrafluoroethylene molds with the test surface of the specimens flush with the surface of the acrylic. The test surfaces were sandblasted.

TABLE 5

Luting cements and metal alloys used in this study.

| | Manufacturers |
| --- | --- |
| Luting cements | |
| DENTSTAT ™ | Ultradent Products, Inc, South Jordan, UT |
| PANAVIA 21 ® | Kuraray Medical Inc., New York, NY |
| GC Fuji Plus | GC America, Inc, Alsip, IL |
| KETAC CEM ™ | 3M/ESPE Corporation, St. Paul, MN |
| ACP C&B | Harry J. Bosworth, Skokie, IL |
| Durelon | 3M/ESPE Corporation, St. Paul, MN |

TABLE 5-continued

Luting cements and metal alloys used in this study.

| | Manufacturers |
|---|---|
| Metal alloys | |
| FIRMILAY ® | Jelenko, San Diego, CA |
| REX4 ™ | Pentron Alloys, LLC, San Diego, CA |
| OLYMPIA ® | Jelenko, San Diego, CA |

A #4 gelatin capsule (Torpac, Inc., Fairfield, N.J.) was half-filled with a resin composite (P60, 3M™/ESPE Corporation, St. Paul, Minn.) and light activated for 20 seconds using a curing light (Spectrum 800, Dentsply/Caulk, Milford, Del.). The remainder of the capsule was filled with the dental luting cement being tested, placed against the metal test surface, and stabilized with finger pressure. Excess material was removed from around the base of the capsule, and the luting cement was allowed to set at room temperature (23±1° C.) for 10 minutes. The specimens were stored in 37±1° C. deionized water for 24 hours before testing.

The specimens were tested to failure in shear with a testing machine (MTS, Alliance RT/5, MTS Corporation, Eden Prairie, Minn.) using a crosshead speed of 0.5 mm/min. Mean shear bond strengths (SBS) and standard deviations were calculated, and means were analyzed statistically using one-way ANOVA and Tukey's Test. The results are presented in the Table 6. The shear bond strengths of DENTSTAT™ to REX4™ and OLYMPIA® were comparable to or greater than those of the other products. Its bond strength to Firmilay was comparable to those of three other cements.

TABLE 6

Shear bond strength means and standard deviations, (MPa), n = 10.

| | Firmilay ® | Rex4 ™ | Olympia ® |
|---|---|---|---|
| DentStat ™ | 4.0 (0.75) C, D | 15.0 (3.65) A | 12.9 (1.33) A |
| Panavia 21 ® | 9.4 (2.70) A | 13.2 (2.60) A | 12.5 (1.63) A |
| GC Fuji Plus | 6.7 (1.91) B | 14.6 (2.17) A | 13.3 (2.00) A |
| Ketac Cem ™ | 4.7 (1.87) B, C | 5.9 (2.13) B | 5.6 (2.10) B |
| ACP C&B | 9.1 (0.94) A | 7.3 (0.45) B | 7.5 (0.40) B |
| Durelon | 5.5 (1.50) B, C | 4.9 (1.13) B, C | 5.7 (1.20) B |
| ZnPO$_4$ | 2.1 (0.68) D | 2.8 (0.51) C | 2.6 (0.41) C |

The SBS of the materials with the same letter within a column are not significantly different (p > 0.05)

Method of Use as Luting Cement for Bonding Orthodontic Brackets to Enamel:

The inventive formulation may also be used as a luting cement for bonding orthodontic brackets to enamel.

EXAMPLE 8

Inventive Formulation Used as a Luting Cement for Bonding Orthodontic Brackets to Enamel The shear bond strengths (SBS) to tooth enamel of DENTSTAT™ and five commercially available orthodontic luting cements were determined. Each brand (Table 7) was designated as an experimental group with ten specimens in each group.

TABLE 7

Orthodontic luting cements used in this study.

| Luting cements | Manufacturers |
|---|---|
| DENTSTAT ™ | Ultradent Products, Inc, South Jordan, UT |
| Transbond XT | 3M/Unitek Monrovia, CA |
| Heliosit | Ivoclar/Vivadent, Schaan, Liechtenstein |
| Aegis Ortho | BOSWORTH ® Co., Skokie, IL |
| GC Fuji LC | GC America Inc, Alsip, IL |
| Ortho Choice | Pulpdent Co. Watertown, MA |

Sixty extracted, noncarious human molar teeth were used for the bond strength test. Surface debris was manually removed from the teeth, and the teeth were stored in a 0.5 per cent aqueous solution of Chloramine-T (Sigma-Aldrich, St. Louis, Mo. 63178) prior to specimen preparation. During specimen fabrication, the enamel surfaces of the teeth were treated following manufacturers' instructions for luting orthodontic brackets. An orthodontic bracket (SYNERGY®, RMO® Roth straight wire, Rocky Mountain Orthodontics, Denver, Colo.) was positioned on the prepared enamel surface with one of the luting cements and photo-cured for 40 seconds (ten seconds on each side of the bracket) using a dental curing light (Spectrum 800, Dentsply/Caulk). The specimens were stored in 37±1° C. deionized water for 24 hours before testing.

The specimens were tested to failure in shear with a testing machine (MTS, Alliance RT/5) using a crosshead speed of 0.5 mm/min. Following shear bond strength testing, all specimens were examined at 8× magnification using a stereomicroscope to determine the mode of failure between the luting cement and enamel. Mean SBS and standard deviations were calculated, and means were analyzed statistically using one-way ANOVA and Tukey's Test.

The results are presented in the Table 8. The shear bond strength of DENTSTAT™ to enamel was significantly higher than those of the other luting cements. All failures were at the cement/enamel interface.

TABLE 8

Shear bond strength to enamel, means (st dev), n = 10.

| | SBS (MPa) |
|---|---|
| DentStat ™ | 12.7 (2.13) A |
| Transbond XT | 11.8 (2.25) B |
| Heliosit | 10.7 (2.88) B |
| Aegis Ortho | 10.6 (1.72) B |
| GC Fugi LC | 9.59 (1.21) B |
| Ortho Choice | 9.39 (1.29) B |

Materials with the same letter are not significantly different (p > 0.05).

Because its superior mechanical properties, the inventive composition may be used in many other dental or biomedical applications, such as stint for stabilizing avulsed, inverted, or luxated teeth, or as bone cement, for bonding implant prostheses and skull implants to bone, or liner and base under amalgam dental restorations.

Obviously, many modifications and variations of the present invention are possible in light of the above teaching. It is therefore to be understood that, within the scope of the appended claims, the invention may be practiced otherwise than as specifically described. The principles described above can be readily modified or adapted for various applications without departing from the generic concept, and therefore such adaptations and modifications are intended to be comprehended within the meaning and range of equivalents of the enclosed embodiments. It is to be understood that the terminology and phraseology herein is for the purpose of description and not of limitation.

What is claimed is:

1. An adhesive composition comprising a mixture of a liquid component and a powder component, wherein
   1) said liquid component comprises 20-50% of hydroxyethyl methacrylate, 10-30% of triethylene glycol dimethacrylate, 5-25% of bis[2-(methacryloyloxy)ethyl] phosphate, 5-25% of dipentaerythritol pentacrylate esters, 5-30% of 2,2-bis[4-(2-hydroxy-3-methacryloxypropoxy) phenyl] propane, 1-8% of ethyl-4-dimethylaminobenzoate-, 0.1-0.8% of camphorquinone and 0.01-0.06% of 2,6-di-tert-butyl-4-methylphenol by weight; and
   2) said powder component comprises 75-95% of glass powder TF grind, 1-5% of a self-curing initiator, 1-5% of 7% silanated 0.7 μm barium glass, and 1-5% of hydrophilic fumed silica having a specific surface area of 200 m$^2$/g by weight.

2. An adhesive composition comprising a liquid component and a powder component, wherein said liquid component comprises 33.68% of hydroxyethyl methacrylate, 20% of triethylene glycol dimethacrylate, 20% of bis[2-(methacryloyloxy)ethyl]phosphate, 10% of dipentaerythritol pentacrylate esters, 10% of 2,2-bis[4-(2-hydroxy-3-methacryloxypropoxy)phenyl]propane, 6% of ethyl-4-dimethylaminobenzoate-, 0.3% of camphorquinone and 0.02% of 2,6-di-tert-butyl-4-methylphenol by weight; and said powder component comprises 93.998% of glass powder TF grind, 2% of a self-curing initiator, 1-2% of 7% silanated 0.7 μm barium glass, and 2% of hydrophilic fumed silica having a specific surface area of 200 m$^2$/g by weight.

3. A method for temporary tooth restoration using adhesive composition of claim 2, comprising:
   1) blending said mixture thoroughly at a powder to liquid ratio of 3:1 by weight;
   2) applying said mixture to a dental substrate; and
   3) allowing said mixture to harden.

4. The method of claim 2, wherein said mixture hardens be in 4 to 4.5 minutes at 37° C.

* * * * *